US008029829B2

(12) United States Patent
Okubo et al.

(10) Patent No.: US 8,029,829 B2
(45) Date of Patent: Oct. 4, 2011

(54) PREVENTIVE, RELIEVING OR THERAPEUTIC COMPOSITION FOR DIABETES MELLITUS AND/OR DIABETIC NEPHROPATHY

(75) Inventors: Tsutomu Okubo, Yokkaichi (JP); Takako Yokozawa, Toyama (JP); Lekh Raj Juneja, Yokkaichi (JP)

(73) Assignee: Taiyo Kagaku Co., Ltd., Yokkaichi-shi (JP)

( * ) Notice: Subject to any disclaimer, the term of this patent is extended or adjusted under 35 U.S.C. 154(b) by 0 days.

(21) Appl. No.: 11/883,356

(22) PCT Filed: Feb. 3, 2005

(86) PCT No.: PCT/JP2005/001618
§ 371 (c)(1),
(2), (4) Date: Jul. 31, 2007

(87) PCT Pub. No.: WO2006/082643
PCT Pub. Date: Aug. 10, 2006

(65) Prior Publication Data
US 2008/0069910 A1   Mar. 20, 2008

(51) Int. Cl.
*A01N 65/00* (2009.01)
(52) U.S. Cl. ........................................ 424/725
(58) Field of Classification Search .................. None
See application file for complete search history.

(56) References Cited

U.S. PATENT DOCUMENTS

| 6,428,818 B1 * | 8/2002 | Morre et al. ............... 424/729 |
| 7,186,824 B2 | 3/2007 | Aga et al. |
| 2002/0055620 A1 | 5/2002 | Aga et al. |
| 2007/0092631 A1 * | 4/2007 | Yokawa et al. ............... 426/656 |

FOREIGN PATENT DOCUMENTS

| EP | 1 129 628 A1 | | 9/2001 |
| JP | 05246859 | * | 9/1993 |
| JP | 6-122626 A | | 5/1994 |
| JP | 6-329541 A | | 11/1994 |
| JP | 11-246417 A | | 9/1999 |
| JP | 11-263795 A | | 9/1999 |
| JP | 2002-68995 A | | 3/2002 |
| JP | 2002-275076 A | | 9/2002 |
| JP | 2003-510286 A | | 3/2003 |
| JP | 2003-313142 A | | 11/2003 |
| JP | 2004-155727 A | | 6/2004 |
| KR | 2002 060395 | * | 7/2002 |
| KR | 2003-56987 | | 7/2003 |
| WO | WO-00/27219 A1 | | 5/2000 |
| WO | WO-01/22981 A1 | | 4/2001 |

OTHER PUBLICATIONS

Journal of Traditional Medicines, vol. 21, Supplement, Aug. 5, 2004, pp. 137.
Certificate of presentation in the 21st Meeting of Medical and Pharmaceutical Society for Wakan-Yaku in Toyama, Aug. 21, 2004.
Journal of BMC Pharmacology, vol. 4(18), Aug. 2004.
Japanese Office Action issued on Dec. 1, 2010 in corresponding Japanese Patent Application No. 2007-501478.

* cited by examiner

*Primary Examiner* — Michael Meller
(74) *Attorney, Agent, or Firm* — Birch, Stewart, Kolasch & Birch, LLP

(57) ABSTRACT

To provide a composition for prevention, amelioration, or treatment of diabetes mellitus and/or diabetic nephropathy, which is less likely to cause any disadvantages such as side effects, and highly safe. [1] A composition for prevention, amelioration, or treatment of diabetes mellitus and/or diabetic nephropathy, containing one or more dietary fiber selected from the group consisting of a degraded galactomannan, an indigestible dextrin, a polydextrose, inulin, arabinogalactan, dietary fiber derived from corn, a water-soluble soybean polysaccharide, psyllium, and a low-molecular weight sodium alginate, and/or a polyphenol compound.

1 Claim, 4 Drawing Sheets

PREVENTIVE, RELIEVING OR THERAPEUTIC COMPOSITION FOR DIABETES MELLITUS AND/OR DIABETIC NEPHROPATHY

TECHNICAL FIELD

The present invention relates to a composition for prevention, amelioration, or treatment, which can be applied to a patient suffering from diabetes mellitus and/or diabetic nephropathy, or human suspected of suffering from the disease.

BACKGROUND ART

Diabetes mellitus has a main feature of a symptom such as polydipsia, polyuria, or weight loss, or a chronic high blood glucose level, which is a disease generally accompanied by complications such as retinopathy, nephropathy, and peripheral nerve disorders. Diabetes mellitus is classified by its causations into primary diabetes mellitus (insulin-dependent diabetes mellitus (type I diabetes mellitus) and non-insulin-dependent diabetes mellitus (type II diabetes mellitus)), secondary diabetes mellitus (pancreatic diabetes mellitus, pancreatic exocrine/endocrine diabetes mellitus, and drug-induced diabetes mellitus), and the like. Further, diabetes mellitus has been known to be a risk factor for an arteriosclerotic disease such as a cardiac infarction or a cerebral infarction.

Conventionally, as a method of treatment of diabetes mellitus, improvement in lifestyle by, for example, a dietetic treatment, a kinesitherapy or the like, and a method of treatment by an insulin injection, a drug administration or the like have been performed. In addition, a substance derived from a plant has been used in the treatment of diabetes mellitus (see, for example, Patent Publication 1).

On the other hand, as a method of treatment of diabetic nephropathy, conventionally, a method of treatment with sulodexide derived from mammalian intestinal mucosa (see Patent Publication 2), efonidipine hydrochloride (see Patent Publication 3), Salviae Miltiorrhizae Radix herb (Patent Publication 4), or the like has been performed.

Patent Publication 1: Japanese Patent Laid-Open No. 2002-068995
Patent Publication 2: Japanese Patent Laid-Open No. Hei 6-329541
Patent Publication 3: Japanese Patent Laid-Open No. Hei 11-246417
Patent Publication 4: Japanese Unexamined Patent Publication No. 2003-510286

DISCLOSURE OF THE INVENTION

Problems to be Solved by the Invention

However, even when the conventional method of treatment is applied, desired effects may not be obtained in some cases. In addition, pharmacotherapy has a disadvantage such as there is a risk of causing side effects besides a therapeutic effect by the drug.

Therefore, an object of the present invention is to provide a composition for prevention, amelioration, or treatment of diabetes mellitus and/or diabetic nephropathy, which is less likely to cause any disadvantages such as side effects, and highly safe.

Means to Solve the Problems

The present invention relates to:
[1] a composition for prevention, amelioration, or treatment of diabetes mellitus and/or diabetic nephropathy, containing one or more dietary fiber selected from the group consisting of a degraded galactomannan, an indigestible dextrin, a polydextrose, inulin, arabinogalactan, dietary fiber derived from corn, a water-soluble soybean polysaccharide, psyllium, and a low-molecular weight sodium alginate, and/or a polyphenol compound;
[2] a composition for prevention, amelioration, or treatment of diabetes mellitus and/or diabetic nephropathy, containing a polyphenol compound, the composition being for use in administration to a patient administered with one or more dietary fiber selected from the group consisting of a degraded galactomannan, an indigestible dextrin, a polydextrose, inulin, arabinogalactan, dietary fiber derived from corn, a water-soluble soybean polysaccharide, psyllium, and a low-molecular weight sodium alginate; and
[3] a composition for prevention, amelioration, or treatment of diabetes mellitus and/or diabetic nephropathy, containing one or more dietary fiber selected from the group consisting of a degraded galactomannan, an indigestible dextrin, a polydextrose, inulin, arabinogalactan, dietary fiber derived from corn, a water-soluble soybean polysaccharide, psyllium, and a low-molecular weight sodium alginate, the composition being for use in administration to a patient administered with a polyphenol compound.

Effects of the Invention

According to the present invention, a composition for prevention, amelioration, or treatment of diabetes mellitus and/or diabetic nephropathy, which is less likely to cause any disadvantages such as side effects caused by the administration, and highly safe, can be provided.

BEST MODE FOR CARRYING OUT THE INVENTION

As a result of intensive studies, the present inventors have found that a composition containing specified dietary fiber and/or a polyphenol compound has a remarkable action of prevention, amelioration, or treatment of diabetes mellitus and/or diabetic nephropathy. The present invention has been perfected thereby.

In other words, one of the features of the composition of the present invention resides in that the composition contains specified dietary fiber and/or a polyphenol compound.

The composition of the present invention is utilizable in the prevention, amelioration, or treatment of any of diabetes mellitus of type I diabetes mellitus and type II diabetes mellitus.

The specified dietary fiber usable in the present invention is one or more dietary fiber selected from the group consisting of a degraded galactomannan, an indigestible dextrin, a polydextrose, inulin, arabinogalactan, dietary fiber derived from corn, a water-soluble soybean polysaccharide, psyllium, and a low-molecular weight sodium alginate, and the degraded galactomannan is preferable, from the viewpoint being originated from a plant belonging to Leguminosae suiting the natural food-oriented consumers, and traditional eating experiences of the consumers as dietary fiber, and further its safety being clarified.

In the present invention, the galactomannan refers to a polysaccharide in which a side chain containing a galactose as a main component thereof is bound to a sugar chain containing mannose as a main component thereof. Specific examples of the galactomannan include guar gum, locust bean gum, tara gum, and the like, and guar gum and locust bean gum are preferable. A commercially available galactomannan includes NEOSOFT G (manufactured by Taiyo Kagaku Co., Ltd.), NEOSOFT L (manufactured by Taiyo Kagaku Co., Ltd.) and the like.

In the present invention, the degraded galactomannan is obtained by mixing one or more of the galactomannans mentioned above and degrading the mixture, or degrading one or more of the galactomannans and mixing the degraded products.

A method for degrading a galactomannan includes, but not particularly limited to, enzymolysis, acidolysis and the like. The enzymolysis is preferred because a product of a certain level of quality is more likely to be obtained. An enzyme usable in enzymolysis may be a commercially available product, or one derived from a natural product, as long as the enzyme is capable of hydrolyzing a sugar chain containing mannose as a main component. The enzyme is preferably a β-galactomannanase derived from a fungus belonging to the genus *Aspergillus* or a fungus belonging to the genus *Rhizopus*, and more preferably a β-galactomannanase derived from the fungus belonging to the genus *Aspergillus*. Here, the enzyme used for the degradation may be used alone or in admixture of two or more kinds.

In a case where a viscosity of a 5% by weight solution of the degraded galactomannan obtained in the manner as mentioned above at 5° C. is determined with a Brookfield viscometer (B-type viscometer), the viscosity is preferably from 5 to 130 mPa·s, more preferably from 5 to 50 mPa·s, and even more preferably from 5 to 20 mPa·s, from the viewpoint of operability upon working and maintenance of therapeutic effects.

In the degraded galactomannan, 80% or more of the sugar chain, this "%" referring to an area ratio in the area under the curve of the high-performance liquid chromatography mentioned below, has a degree of mannose polymerization of preferably from 22 to 47 units, more preferably a degree of mannose polymerization of from 30 to 42 units, and even more preferably a degree of mannose polymerization of from 32 to 40 units, from the viewpoint of maintaining therapeutic effects. Here, the degree of mannose polymerization is determined by dissolving a degraded galactomannan in water, and subjecting the solution to high-performance liquid chromatography with G3000PW (manufactured by Tosoh Corporation). As standard reagents of the sugar chain units at this time, straight-chained dextrins having known degrees of glucose polymerization (degrees of glucose polymerization: 50, 100, and 150) are used.

In addition, the weight-average molecular weight of the degraded galactomannan is preferably from 3,000 to 100,000, more preferably from 5,000 to 50,000, and even more preferably from 10,000 to 30,000, from the viewpoint of maintaining therapeutic effects. Here, the weight-average molecular weight can be obtained by subjecting a degraded galactomannan to high-performance liquid chromatography (column manufactured by YMC Co., Ltd.: YMC-Pack Diol-120) using polyethylene glycols (molecular weights: 2,000, 20,000 and 200,000) as molecular weight markers to obtain its molecular weight distribution, numerically converting the molecular weight distribution by applying it to a calibration curve obtained from the molecular weight markers, and averaging the resulting values.

Further, the fiber content of the degraded galactomannan, when determined according to Official Method of AOAC (*Official Methods of Analysis of AOAC INTERNATIONAL*, 16*th Edition*, Volume II, Chapter 32, p. 7), is preferably 60% by weight or more, more preferably 65% by weight or more, and even more preferably 75% by weight or more, from the viewpoint of even more enhancing the effects of the present invention.

By the procedures described above, a degraded galactomannan can be obtained. The resulting degraded product can be used as it is, or can be used after washing with water or the like as desired. In addition, a commercially available product can be used. A commercially available product includes, for example, SUNFIBER (manufactured by Taiyo Kagaku Co., Ltd.), FIBERON (manufactured by DAINIPPON PHARMACEUTICAL CO., LTD.) and the like.

Commercially available products of the indigestible dextrin include, for example, Fibersol-2 (manufactured by Matsutani Chemical Industry Co., Ltd.), Pinefiber (manufactured by Matsutani Chemical Industry Co., Ltd.), and Nutriose (manufactured by ROQUETTE). Commercially available products of the polydextrose include, for example, Litesse (manufactured by DANISCO JAPAN LTD.), Litesse II (manufactured by DANISCO JAPAN LTD.), Litesse III (manufactured by DANISCO JAPAN LTD.), and STA-LITE III (manufactured by A. E. STALEY MFG. Co.). Commercially available products of the inulin include, for example, Raftiline (manufactured by Nihon Sibert Hegner K.K.), Raftilose (manufactured by Nihon Sibert Hegner K.K.), and Fuji FF (manufactured by Fuji Nihon Seito Corporation). Commercially available products of the arabinogalactan include, for example, FIBERAID (manufactured by MRC POLYSACCHARIDE CO., LTD.) and Arabinogalactan (manufactured by CHEMICAL BIOLOGY INSTITUTE (CBI)). Commercially available products of the dietary fiber derived from corn include, for example, Suiyousei Kohn Faibah (manufactured by NIHON SHOKUHIN KAKO CO., LTD.), NISSHOKU ARABINOXYLAN (manufactured by SHOKUHIN KAKO CO., LTD.), and Toumorokoshi Shokumotsu Senni (manufactured by Fuji Sangyo). Commercially available products of the water-soluble soybean polysaccharide include, for example, SOYAFIBE (manufactured by Fuji Oil Co. Ltd.) and SM-700 (manufactured by San-Ei Gen F. F. I., Inc.). Commercially available products of the psyllium include, for example, Psyllium 80PS (manufactured by Bizen Chemical Co., Ltd.) and Psyllium Seed Gum (manufactured by SHIKISHIMA BOSEKI K.K.). Commercially available products of the low-molecular weight sodium alginate include, for example, SOLGIN (manufactured by Kaigen Co., Ltd.).

The content of the above-mentioned dietary fiber in the composition of the present invention is such that in a case where the dietary fiber is used alone, the content of the dietary fiber is preferably from 60 to 95% by weight, and more preferably 70 to 90% by weight, and that in a case where the dietary fiber is used as a mixture with a polyphenol compound mentioned below, the content of the dietary fiber is preferably from 20 to 80% by weight, and more preferably 40 to 60% by weight, from the viewpoint of reducing hygroscopicity due to impurities such as a monosaccharide.

The polyphenol compound usable in the present invention is preferably, but not particularly limited to, a polyphenol compound derived from a plant belonging to Theaceae, cocoa, grape seeds, sweet potato or red wine. There may be used a plant as it is, an extract from a plant, or an extract residue, or alternatively a chemically synthesized product may be used. The extract from a plant includes hot-water extract fractions, solvent extract fractions obtained by an organic solvent, such as an alcohol, ethyl acetate or a petroleum ether, steam distillation fractions, compressed fractions, fractions obtained by oil adsorption, fractions obtained by liquefied gas extraction, supercritical extraction fractions, or dry distillation fractions. Among them, a polyphenol compound obtained from a hot-water extract fraction of the plant belonging to Theaceae is more preferable, from the viewpoint of the proportion of a compositional ratio of the polyphenol compound.

Among the plants belonging to Theaceae, tea (*Camellia sinensis* L.) is preferable. Among them, the polyphenol compound is preferably an extract from green tea, oolong tea or black tea, and especially an extract from green tea is preferable. The above-mentioned hot-water extract fraction can be prepared, for example, by a process described in Japanese Patent Laid-Open No. Hei 8-103225. An extract obtained by removing caffeine from the extract of green tea with column chromatography is even more preferable, from the viewpoint of reducing side effects caused by caffeine without blocking therapeutic effects. The content of the polyphenol compound, on a dry basis, is preferably 70% by weight or more, more preferably 75% by weight or more, and even more preferably 80% by weight or more, of the tea extract, from the viewpoint of preventing the flavor from being lessened when used in foods. The content can be determined according to the method described in the following Examples. The content of the caffeine, on a dry basis, is preferably 1.5% by weight or less, more preferably 1.0% by weight or less, and even more preferably 0.5% by weight or less, of the tea extract, from the viewpoint of reducing side effects caused by caffeine without blocking therapeutic effects.

Specific examples of the above-mentioned polyphenol compound include, for example, (+)-catechin, (+)-gallocatechin, (−)-gallocatechin gallate, (−)-epicatechin, (−)-epicatechin gallate, (−)-epigallocatechin, (−)-epigallocatechin gallate, gallic acid, free theaflavin, theaflavin monogallate A, theaflavin monogallate B, theaflavin digallate, and the like. The above-mentioned polyphenol compounds can be used alone or in a mixture. Among the above-mentioned polyphenol compounds, at least one polyphenol compound selected from the group consisting of (−)-gallocatechin gallate, (−)-epicatechin gallate, and (−)-epigallocatechin gallate is preferable.

When the above-mentioned polyphenol compounds are mixed and the mixture is used, it is preferable that the content of each polyphenol compound in the polyphenol compound mixture is as follows: (+)-catechin: 0.2 to 5.0% by weight, (+)-gallocatechin: 0.5 to 10.0% by weight, (−)-gallocatechin gallate: 3.0 to 8.0% by weight, (−)-epicatechin: 3.0 to 10.0% by weight, (−)-epicatechin gallate: 5.0 to 15.0% by weight, (−)-epigallocatechin: 2.0 to 18.0% by weight, (−)-epigallocatechin gallate: 25.0 to 75.0% by weight, gallic acid: 0 to 2.0% by weight, free theaflavin: 0 to 20.0% by weight, theaflavin monogallate A: 0 to 5.0% by weight, theaflavin monogallate B: 0 to 5.0% by weight, and theaflavin digallate: 0 to 5.0% by weight.

The content of the polyphenol compound in the composition of the present invention is such that in a case where the polyphenol compound is used alone, the content of the polyphenol compound is preferably from 50 to 95% by weight, and more preferably from 70 to 90% by weight, or that in a case where the polyphenol compound is mixed with the dietary fiber mentioned above and the mixture is used, the content of the polyphenol compound is preferably from 20 to 80% by weight, and more preferably from 40 to 60% by weight, from the viewpoint of reducing side effects by caffeine, exhibiting the effects, and the like.

In the case where the dietary fiber and the polyphenol compound mentioned above are both contained in the composition of the present invention, the mixing ratio of the dietary fiber and the polyphenol compound, i.e. dietary fiber/polyphenol compound (weight ratio), is preferably from 1/5 to 5/1, more preferably from 1/3 to 3/1, and even more preferably from 1/2 to 2/1.

Since the dietary fiber and the polyphenol compound mentioned above are both contained in the composition of the present invention, the composition exhibits an even more excellent effect for prevention, amelioration, or treatment of diabetes mellitus and/or diabetic nephropathy.

In addition, as the composition of the present invention, a food or a medicament is preferable, from the viewpoint of being suitable for daily use.

The food included in the present invention includes solid foods such as dry foods and supplements, and liquid foods such as soft drinks, mineral water, luxury beverages and alcoholic beverages. Specifically, the solid food includes, but not particularly limited to, paste products, processed soy products, seasonings, mousse, jelly, cold confectioneries, candies, chocolates, gum, crackers, cake, bread and the like. In addition, the liquid food includes, but not particularly limited to, teas such as green tea, oolong tea, black tea and herb tea, fruit juice concentrates, reconstituted juice concentrates, fresh juices, mixed fruit juices, fruit grain-containing fruit juice, fruit juice-containing beverages, mixed fruit and vegetable juice, vegetable juice, carbonated beverages, soft drinks, milk beverage, Japanese sake, beer, wine, cocktails, shochu, whiskey, and the like. The food included in the present invention also includes nutritional foods, dietary supplements, and the like, each containing various nutrients such as amino acids, proteins, and minerals. Further, the food included in the present invention includes a therapeutic diet such as a liquid diet; a diet for controlling toromi (texture of a food slightly thicker than a soupy state that enables easier deglutition); a therapeutic dietary supplement such as a dietary supplement for deglutition; a therapeutic auxiliary such as an agent for controlling toromi, a texture improver for deglutition of a diet and a viscosity controlling agent, and the like.

In addition, the medicament included in the present invention may be in any forms of a solution, a suspension, a powder, and a solid molded product, and the preparation form thereof includes a tablet, a capsule, a powder, a granule, a drinkable preparation, an injection, a patch, a suppository, an inhalant, and the like.

As the method for producing the composition of the present invention, a general method for producing a food or medicament can be applied.

The dose of the composition of the present invention for obtaining the desired effects of the present invention is such an amount that the dietary fiber is preferably from 0.3 to 10 g/day, and more preferably from 0.5 to 5 g/day, and that the polyphenol compound is preferably from 0.1 to 3 g/day, and more preferably from 0.2 to 1.5 g/day. However, since there are individual differences (degree of severity of the disease, sex, age, and the like), the dose in the present invention is not limited to the above range, and the dose may be properly set specifically for each individual so as to obtain the desired effects of the present invention.

The method of administering the composition of the present invention is not particularly limited, and the method of administration is preferably oral administration, intravenous administration, or transrectal administration, and the oral administration is more preferable. The administration may be carried out within the preferred range mentioned above.

When the composition of the present invention is administered to a patient, either of the above-mentioned dietary fiber or the above-mentioned polyphenol compound may be administered alone to a patient; both the dietary fiber and the polyphenol compound may be simultaneously administered to a patient; the dietary fiber may be administered to a patient, and the polyphenol compound may be additionally administered to the patient; or, alternatively, the polyphenol compound may be administered to a patient, and the dietary fiber may be additionally administered to the patient.

Further, the composition of the present invention can be used together with a conventional therapeutic agent for diabetes mellitus or diabetic nephropathy.

By using the composition of the present invention, it has been found that decreases in a glucose concentration level in blood, an amount of glycosylated protein, a urea nitrogen concentration level, a triglyceride concentration level, a creatinine concentration level, an MDA concentration level, and an amount of urinary protein are caused in rats with diabetic nephropathy. In addition, by using the composition of the present invention, ameliorative actions in exudative lesion, arteriolosclerosis, and proliferation in mesangial substrate have been found in glomeruli of rats with diabetic nephropathy. According to the composition of the present invention, it has been found that a decrease in a blood glucose level, an increase in an insulin blood concentration level, and a decrease in a lipid level are caused in patients with type I diabetes mellitus or patients with type II diabetes mellitus. Therefore, the composition of the present invention can be used for the prevention, amelioration, and treatment of diabetes mellitus or diabetic nephropathy.

The present invention will be specifically described hereinbelow by Examples and Test Examples, without intending to limit the scope of the present invention thereto.

EXAMPLES

Example 1

One-hundred parts by weight of guar gum powder was added to 898 parts by weight of water, and mixed, and a pH of the mixture was adjusted to 3.0 with a 10% by weight aqueous citric acid solution. To this mixture was added a mixture of 0.2 parts by weight of β-galactomannase derived from a fungus belonging to the genus *Aspergillus* (manufactured by Novo Nordisk Bioindustry, Ltd., trade name: Viscozyme, 1,000 units) and 2 parts by weight of water, and the mixture was allowed to cause enzyme reaction at 40° to 45° C. for 24 hours. After the termination of the reaction, the reaction mixture was heated at 90° C. for 15 minutes to deactivate the enzyme. The reaction mixture was filtered to remove insoluble substances, and the resulting transparent solution was concentrated under a reduced pressure. The resulting concentrate (solid content: 20%) was spray-dried, to give 65 parts by weight of a white powder of polygalactomannan.

The weight-average molecular weight, the degree of mannose polymerization, the viscosity, and the fiber content for the resulting degraded galactomannan were determined in the following manner.

Weight-Average Molecular Weight

The weight-average molecular weight was determined by dissolving a degraded galactomannan in water to prepare an aqueous solution having a concentration of 0.5 (w/v) %, and subjecting the aqueous solution to high-performance liquid chromatography (column: YMC-Pack Diol-120, manufactured by YMC) using polyethylene glycols (molecular weight: 2,000, 20,000, 100,000 and the like) as markers.

Degree of Mannose Polymerization

The degree of mannose polymerization was determined according to high-performance liquid chromatography (flow rate: 1.0 ml/min, 40° C., eluent: 0.2 M phosphate buffer (pH 6.9)) using a column G3000PW (manufactured by Tosoh Corporation) as a fixed bed. As a result, 80% or more of the sugar chain of the degraded galactomannan had a degree of mannose polymerization within the range of from 30 to 40 units. At this time, as standard reagents for the sugar chain units, straight-chain dextrins having known degrees of glucose polymerization (degrees of glucose polymerization: 50, 100, and 150) were used.

Viscosity

The viscosity was determined by dissolving a degraded galactomannan in water to prepare an aqueous solution having a concentration of 0.5 (w/v) %, and measuring a viscosity of the aqueous solution with a B-type viscometer (manufactured by TOKI SANGYO CO., LTD.) at 5° C.

Fiber Content

The fiber content of the degraded galactomannan was determined according to AOAC Official Method (*Official Methods of Analysis of AOAC INTERNATIONAL*, 16th Edition, Volume II, Chapter 32, p. 7).

The resulting degraded galactomannan had a weight-average molecular weight, a degree of mannose polymerization, a viscosity, and a fiber content of 20,000, 30 to 40 units, 13 mPa·s and 75% by weight, respectively.

Example 2

About 1500 L of water added to 1,000 kg of green tea (*Camellia sinensis* L.) while stirring, and the extraction was carried out at 80° C. for 3 hours. The extract was filtered, and a filtrate was obtained. This filtrate was distributed with ethyl acetate, and the ethyl acetate was evaporated away, to give 100 kg of a polyphenol compound.

The contents of the resulting polyphenol compounds were as follows: (+)-catechin: 0.6% by weight, (+)-gallocatechin: 4.6% by weight, (−)-gallocatechin gallate: 6.3% by weight, (−)-epicatechin: 6.5% by weight, (−)-epicatechin gallate: 9.8% by weight, (−)-epigallocatechin: 14.5% by weight, (−)-epigallocatechin gallate: 45.8% by weight, and gallic acid: 0.5% by weight. In addition, the content of the total polyphenol compounds was 85.7% by weight, and that of caffeine was 0.1% by weight.

Test Example 1

Wistar male rats (body weight: 120 to 130 g, purchased from Nippon SLC) were used. A wire-bottom cage kept at a room temperature of 25° C. and humidity of about 60% was used. The illumination conditions were set at 12 hours light and 12 hours darkness. As an experimental feed, those manufactured by CLEA containing 24.0% by weight proteins/3.5% by weight lipids/60.5% by weight carbohydrates, and water was given ad libitum, and allowed to adapt thereto for several days. Thereafter, the rats were fasted overnight, and intraperitoneally injected with 50 mg/kg Streptozotocin (STZ, manufactured by Sigma) dissolved in a citrate buffer, thereby generating diabetes mellitus-induced rats.

After one week passed from the injection, the diabetes mellitus-induced rats were orally administered for 50 consecutive days with the compositions and the Test Groups shown in Table 1, using as dietary fiber the degraded galactomannan prepared in Example 1, an indigestible dextrin (manufactured by Matsutani Chemical Industry Co., Ltd., trade name: Fibersol-2), a polydextrose (manufactured by CULTOR FOOD SCIENCE, INC., trade name: Litesse), inulin (manufactured by Nihon Sibert Hegner K.K., trade name: Raftiline), arabinogalactan (manufactured by MRC POLYSACCHARIDE CO., LTD., trade name: FIBERAID), dietary fiber derived from corn (manufactured by NIHON SHOKUHIN KAKO CO., LTD., trade name: Water-Soluble Corn Fiber), a water-soluble soybean polysaccharide (manufactured by Fuji Oil Co. Ltd., trade name: SOYAFIBE), psyllium (manufactured by Bizen Chemical Co., Ltd., trade name: Psyllium 80PS), a low-molecular weight sodium alginate (manufactured by Kaigen Co., Ltd., trade name: SOLGIN), and using as a polyphenol compound the polyphenol compound prepared in Example 2.

TABLE 1

| Test Group | Dose of Test Substance(s) |
|---|---|
| Control Group | Physiological Saline 1 g/kg BW/day |
| Group A | Degraded Galactomannan of Ex. 1 50 mg/kg BW/day + Polyphenol Compound of Ex. 2 50 mg/kg BW/day |
| Group B | Indigestible Dextrin 100 mg/kg BW/day + Polyphenol Compound of Ex. 2 50 mg/kg BW/day |
| Group C | Polydextrose 100 mg/kg BW/day + Polyphenol Compound of Ex. 2 50 mg/kg BW/day |
| Group D | Inulin 100 mg/kg BW/day + Polyphenol Compound of Ex. 2 50 mg/kg BW/day |
| Group E | Arabinogalactan 100 mg/kg BW/day + Polyphenol Compound of Ex. 2 50 mg/kg BW/day |
| Group F | Dietary Fiber Derived from Corn 100 mg/kg BW/day + Polyphenol Compound of Ex. 2 50 mg/kg BW/day |
| Group G | Water-Soluble Soybean Polysaccharide 100 mg/kg BW/day + Polyphenol Compound of Ex. 2 50 mg/kg BW/day |
| Group H | Psyllium 100 mg/kg BW/day + Polyphenol Compound of Ex. 2 50 mg/kg BW/day |
| Group I | Low-Molecular Weight Sodium Alginate 100 mg/kg BW/day + Polyphenol Compound of Ex. 2 50 mg/kg BW/day |

On the 50th day of the administration of the test substance, the blood was collected, sera were separated, and the glucose concentration level, the amount of glycosylated protein, and the creatinine concentration level in sera were determined. The results are shown in Table 2.

Here, the glucose concentration level, the amount of glycosylated protein, and the creatinine concentration level were determined by using the following methods.

Glucose Concentration Level

In the determination of the glucose concentration level, Glucose CII Test Kit (manufactured by Wako Pure Chemical Industries Ltd.) was used. The glucose level in the liver or the kidney was determined by disrupting each tissue with 9 times the volume of an ice-cooled physiological saline containing 0.15 M $Ba(OH)_2$ and 5% by weight of $ZnSO_4$, centrifuging the disruption (3000 rpm, 15 minutes), and determining the glucose level for the supernatant (0.5 mL) with the above kit.

Amount of Glycosylated Protein

The extent of glycosylation of the protein was evaluated by determining the glucose non-enzymatically linked to the protein released as 5-hydroxymethyl furfural (5-HMF). In other words, in accordance with the methods of Fluckiger and Winterhalter, 0.1 mL of sera were diluted to a volume of 1.0 mL, the dilution was mixed with 0.5 mL of 0.1 M oxalic acid, and the mixture was hydrolyzed at 100° C. for 4.5 hours. Thereafter, the hydrolyzed mixture was reacted with thiobarbituric acid (TBA), and absorbance at 443 nm of the reaction mixture was determined.

Creatinine Concentration Level

The creatinine concentration level was determined using CRE-EN Kainos (manufactured by Kainos Laboratories Inc.).

TABLE 2

| Test Group | Glucose Concentration Level (mg/dL) | Amount of Glucosylated Protein (nmol/mg Protein) | Creatinine Concentration Level (mg/dL) |
|---|---|---|---|
| Control Group | 667.0 ± 39.5 | 29.8 ± 0.9 | 0.506 ± 0.007 |
| Group A | 538.3 ± 21.8* | 26.1 ± 0.7* | 0.433 ± 0.003* |
| Group B | 540.0 ± 28.7* | 27.2 ± 0.8* | 0.436 ± 0.009* |
| Group C | 539.8 ± 25.4* | 27.1 ± 0.5* | 0.440 ± 0.008* |
| Group D | 538.4 ± 22.6* | 26.3 ± 0.8* | 0.435 ± 0.010* |
| Group E | 540.1 ± 23.5* | 26.9 ± 0.6* | 0.438 ± 0.003* |
| Group F | 541.1 ± 22.3* | 26.7 ± 0.5* | 0.433 ± 0.005* |
| Group G | 539.6 ± 20.0* | 27.0 ± 0.5* | 0.441 ± 0.007* |
| Group H | 538.6 ± 22.5* | 27.2 ± 0.6* | 0.448 ± 0.002* |
| Group I | 539.7 ± 23.9* | 26.9 ± 0.8* | 0.435 ± 0.007* |

*$p < 0.001$ vs. Control Group

As shown in Table 2, it could be seen that Groups A to I administered with the inventive products have the lowering of the glucose concentration levels and the amounts of the glycosylated protein, thereby showing ameliorative effects for diabetes mellitus, and have the lowering of the creatinine concentration levels, thereby suppressing diabetic nephropathy, which is a complication of diabetes mellitus.

Test Example 2

In order to examine a therapeutic effect of a test drug for patients with non-insulin-dependent diabetes mellitus (NIDD), the oral glucose tolerance test and the insulin release test were carried out for a total of 30 patients with NIDD.

As tested subjects, 30 patients who received treatment consecutively for sixty days or more of the patients with type II diabetes mellitus, the patients who had treatment at a hospital, were used. As a test substance, each patient was asked to take 0.4 g of the degraded galactomannan prepared in Example 1 and 50 mg of the polyphenol compound prepared in Example 2, per meal, for each of three meals.

The criteria of selection of the subjects were considered according to the diagnostic criteria of the WHO in the year 1998, as those cases in which the subjects satisfied one of the following items:

(1) as a result of the determination of the blood glucose level in the vein, individuals show a fasting blood glucose level of 7.8 mmol/L (140 mg/dl) or more, or a postprandial blood glucose level of 11.1 mmol/L (200 mg/dl) or more;

(2) even while individuals show a fasting blood glucose level of 7.8 mmol/L (140 mg/dl) or less, individuals show a blood glucose level of 11.1 mmol/L (200 mg/dl) or more as a result of an oral glucose tolerance test; and (3) an oral glucose tolerance test is conducted, and individuals show a one-hour postprandial blood glucose level and a two-hour postprandial blood glucose level of each being 11.1 mmol/L (200 mg/dl) or more, or a fasting blood glucose level of 7.8 mmol/L (140 mg/dl) or more.

The criteria for the failure of the subjects were defined as subjects that satisfied the following cases, among the individuals satisfying the above criteria for selection:

(1) while individuals show a blood glucose level before giving a test drug satisfying the criteria of selection, the individuals show a fasting blood glucose level through kinesitherapy or dietetic treatment of 7.8 mmol/L (140 mg/dl) or less, or individuals show a 2-hour postprandial blood glucose level of 11.1 mmol/L (200 mg/dl) or more;

(2) individuals violate the test rule in a manner that would influence the measured results;

(3) individuals are diagnosed as patients with insulin-dependent diabetes mellitus (type I diabetes mellitus);

(4) individuals are judged as patients with diabetic ketosis or patients with acidosis within one month from the disclosure of the test;

(5) individuals have severe complications, or patients with psychosis;

(6) individuals have discontinued the treatment, or individuals are aberrant in the medical records; and (7) individuals of ages 15 or under, or pregnant individuals or women in the state of maternity.

The observation methods were in accordance with the followings.

1) General Observations

General physical examinations, such as blood glucose levels for each of subjects, and lipid levels in the heart, the kidneys, the liver, and the blood for a part of the applicable patients are determined and recorded.

2) Determinations of Effects (1) determination of a fasting blood glucose level and a 2-hour postprandial blood glucose level (determined every 10 to 15 days after the disclosure of the administered drug);

(2) oral glucose tolerance test;

(3) insulin release test;

(4) determination of amino-fructose in blood

The item (1) mentioned above was mandatorily determined, and all the other items were determined as occasion demands. Thereafter, the found values after 60 days from the administration were compared with those found values before the test.

The judgment criteria were the followings:

1) Remarkable

In a case where basic symptoms disappearing after the administration of the drug, and at the same time a fasting blood glucose level being 7.2 mmol/L (130 mg/dl) or less, and a 2-hour postprandial blood glucose level, after the patients are allowed to take a meal, being 8.3 mmol/L (150 mg/dl) or less; or a blood glucose level or a urinary glucose level is reduced by 30% or more that of the level before the treatment 2) Effective In a case where symptoms being ameliorated after the administration of the drug, and at the same time a fasting blood glucose level being 8.3 mmol/L (150 mg/dl) or less, and a 2-hour postprandial blood glucose level, after the patients are allowed to take a meal, being 10 mmol/L (180 mg/dl) or less; or a blood glucose level or a urinary glucose level is reduced by 10% or more that of the level before the treatment 3) Non-Effective symptoms not being ameliorated after the administration of the drug, and the degree of a decrease in a blood glucose level or a urinary glucose level not reaching the above standard level The results of the above clinical tests are shown hereinbelow.

1. Decrease in Blood Glucose Level

Of the total of 30 patients with type II diabetes mellitus, the effects were remarkable in 21 cases (71.2%), effective in 8 cases (26.3%), and non-effective in 1 case (2.48%), so that a total effective percentage was found to be 97.5%.

2. Percentage of Decrease in Blood Glucose Level

Of the 30 subjects, 25 cases (82.2%) showed a decrease in a blood glucose level by 30% or more, and 4 cases (15.2%) showed a decrease in a blood glucose level by 10% or more. There was one case where the blood glucose level was increased without showing a decrease in a blood glucose level after the treatment. However, the blood glucose levels of individuals showing a decrease in a blood glucose level by 30% or more were determined. As a result, there were 4 cases showing a blood glucose level of 7.2 mmol/L (130 mg/dl) or more, and these cases were judged as being effective, instead of being judged as remarkable.

3. Average Period for Decrease in Blood Glucose Level

An average period required for a decrease in a blood glucose level in 30 cases was 40.9 days.

Test Example 3

In order to examine a therapeutic effect of the composition according to the present invention for non-insulin-dependent diabetes mellitus, 24 patients with type II diabetes mellitus were selected, and a sample was administered to each patient. Changes in blood glucose levels, confirmation of amount of insulin release, and blood lipid concentration levels were measured before and after the administrations. As test substances, the patients were asked to take 0.4 g of the degraded galactomannan prepared in Example 1 and 50 mg of the polyphenol compound prepared in Example 2 per meal for each of three meals.

Here, the selection of the subjects was made in accordance with Test Example 2.

The determination methods were carried out in accordance with the followings.

1) Administration period: Fifty days from the administration was defined as a treatment period.

2) Timing of determination: During the period of treatment, the blood glucose level was determined every Monday, and fasting blood glucose levels before the disclosure of the administration of the drug and after 60 days from the administration of the drug were determined, and the blood insulin concentration levels were determined one hour and two hours after a meal.

3) Measurement device: A one-touch blood glucose level measurement device from Johnson & Johnson, U.S.A. was used, and Preimmune Counter Observation Set was used for the blood insulin concentration level.

4) Administration method: Subjects were divided into two groups of 12 individuals each for each of Test Group and Control Group, in which the subjects in the Test Group were orally administered with a test substance and a commercially available therapeutic agent for diabetes mellitus, and the subjects in the Control Group were orally administered with the commercially available therapeutic agent for diabetes mellitus.

5) Determination Method: During the period of before and after the treatment, symptoms, blood pressures, and body weights were determined every week, and serum glucose concentration levels (blood glucose levels), insulin concentration levels, total cholesterol (TC) concentration levels and neutral lipid (TG) concentration levels, and urinary glucose concentration levels (urinary glucose levels) were each determined using an enzyme method upon fasting and two hours after a meal.

Here, the glucose concentration level was determined in accordance with the method as mentioned above, and the insulin concentration level, the total cholesterol (TC) concentration level and the neutral lipid (TG) concentration level, and the urinary glucose concentration level were determined using the following methods.

Insulin Concentration Level

The insulin concentration level was determined with Insulin Assay Kit (manufactured by Berthold, Japan).

Total Cholesterol Concentration Level

The total cholesterol concentration level was determined with CHOLESTEROL E-Test Wako (manufactured by Wako Pure Chemical Industries, Ltd.).

Neutral Lipid Concentration Level

The neutral lipid concentration level was determined with TRIGLYCERIDE E-Test Wako (manufactured by Wako Pure Chemical Industries, Ltd.).

Urinary Glucose Concentration Level

The urinary glucose concentration level was determined in the same manner as above except that urine was used in place of sera.

The results are shown hereinbelow.

1. Judgment Criteria

1) Excellent

In a case where basic symptoms disappearing after the administration of the drug, and at the same time a fasting blood glucose level being 7.2 mmol/L (130 mg/dl) or less, and a 2-hour postprandial blood glucose level, after the patients are allowed to take a meal, being 8.3 mmol/L (150 mg/dl) or less; or a blood glucose level or a urinary glucose level is reduced by 30% or more that of the level before the treatment 2) Effective In a case where symptoms being ameliorated after the administration of the drug, and at the same time a fasting blood glucose level being 8.3 mmol/L (150 mg/dl) or less, and a 2-hour postprandial blood glucose level, after the patients are allowed to take a meal, being 10 mmol/L (180 mg/dl) or less; or a blood glucose level or a urinary glucose level is reduced by 10% or more that of the level before the treatment.

2. Effects

Blood glucose levels of the Test Group and the Control Group were remarkably lowered ($p<0.01$). In the cases of the Test Group (12 cases), 7 cases were found to be 'excellent' and 4 cases 'effective,' whereas in the cases of the Control Group, 4 cases were found to be 'excellent' and 4 cases 'effective,' whereby giving total effective percentages of 91.67% and 66.7%, respectively, thereby confirming that the Test Group gave an even higher effect for a decrease in blood glucose levels than the Control Group. Also, in the period required for the decrease in glucose levels, the Test Group took 20.15 days, as compared to 26.93 days of the Control Group, so that a more excellent therapeutic effect of the test drug was found.

3. Changes in Blood Insulin Concentration Levels

Blood insulin concentration levels were determined upon fasting before and after the treatment, and one hour and two hours after a meal for each of 12 cases of the Test Group. There were no specific changes before and after the treatment ($p>0.05$) in the blood insulin concentration levels determined upon fasting and two hours after the meal. However, the blood insulin concentration levels determined one hour after the meal showed a dramatic increase. The results are shown in Table 3.

4. Changes in Lipid Levels

The blood TC concentration levels and the blood TG concentration levels of the Test Group and the Control Group were determined. As a result, the TC and TG concentration levels in the Test Group were remarkably low. The results are shown in Table 3.

TABLE 3

| | Insulin in Blood (mmol/L) | | | Lipid in Blood (mmol/L) | |
|---|---|---|---|---|---|
| | Fasting | One Hour after Meal | Two Hours after Meal | TC | TG |
| Control Group | 10.05 ± 3.98 | 41.55 ± 7.22 | 75.66 ± 14.95 | 6.88 ± 0.69 | 2.81 ± 0.66 |
| Test Group | 10.78 ± 3.90 | 87.29 ± 13.90 | 97.88 ± 21.15 | 5.12 ± 0.50 | 1.19 ± 0.31 |

5. Amelioration of Symptoms

In the patients of the Test Group, there were no longer symptoms of polydipsia, polyuria, and polyphagia, so that the physical capacity was also remarkably improved. In the complications of skin, or the like (4 cases), the disappearances of symptoms (3 cases) were confirmed. Required matters for the patients with diabetes mellitus include regulation of blood glucose levels, and recovery to functions and physical dispositions of normal individuals. According to the present experiment, it was judged that the sample of the present invention sufficiently solved the disadvantages mentioned above.

Test Example 4

Examples of Administration to Patients with Insulin-Dependent Diabetes Mellitus (Type I Diabetes Mellitus)

Case 1

1) Outline History of the Patient

Fifty-eight year-old female; symptoms of polydipsia, polyuria, and polyphagia began to appear in the year 1992, and her body weight dramatically reduced from 68 kg to 61 kg in a period of 2 months. She was diagnosed as diabetes mellitus upon visiting a hospital, and hospitalized for forty days in the year 1998 due to a dramatic increase in blood glucose level (the level being 280 mg/dl upon fasting) and complications such as vision loss. After leaving the hospital, she was administered with insulin in an amount of 20 units each, and the fasting blood glucose level during the administration of insulin was from 180 to 200 mg/dl.

2) Administration

After having obtained the consent of the patient herself and her family members, the patient was asked to take 0.4 g of the degraded galactomannan prepared in Example 1 and 50 mg of the polyphenol compound prepared in Example 2 in each of three meals. After having taken the above for 3 weeks, the blood glucose level was ameliorated to 138 mg/dl, and an insulin dose was reduced to 15 units. After an additional week, the blood glucose level was determined again. As a result, the found value was 140 mg/dl, and an insulin dose was reduced to 5 units. After having taken the above in the same manner, the administration of insulin was discontinued on the sixth week, but a fasting blood glucose level was maintained at a level of from 140 to 180 mg/dl. In addition, the lowering of vision was ameliorated.

Case 2

1) Outline History of the Patient

A woman born in the year 1937. She was diagnosed to be type I diabetes mellitus in a physical examination upon retirement from the company 10 years before. Since then, by a regular administration of insulin (3 times a day, 10 units per dose), an ambulatory (outpatient) treatment, and the like, she had an average fasting blood glucose level measured before the administration of the inventive product of from 210 to 230 mg/dl. She had no records of hospitalization, and symptoms of polydipsia, polyuria, and polyphagia, weight loss, or complications due to diabetes mellitus were not found; however, rubor, pruritus, or hypertrophy of injected sites had became markedly notable due to the regular administration of insulin.

2) Administration

After having obtained the consent of the patient herself and her family members, the patient was asked to take 0.4 g of the degraded galactomannan prepared in Example 1 and 50 mg of the polyphenol compound prepared in Example 2 in each of three meals. As a result of the measurement of the blood glucose levels, if the level of 180 mg/dl was maintained, it was recommended to reduce an insulin dose by 5 units each. After having taken the above for five weeks, the blood glucose level was ameliorated to a level of from 132 to 167 mg/dl, and an insulin dose was reduced by 5 units each for each administration. It was found that side effects such as rubor, pruritus, and hypertrophy were ameliorated.

Test Example 5

Wistar male rats (body weight: 120 to 130 g, purchased from Nippon SLC) were used. A wire-bottom cage kept at a room temperature of 25° C. and humidity of about 60% was used. The illumination conditions were 12 hours light and 12 hours darkness. As an experimental feed, a product manufactured by CLEA, containing 24.0% by weight proteins/3.5% by weight lipids/60.5% by weight carbohydrates. The rats were given water ad libitum, and allowed to adapt thereto for several days. Thereafter, 3/4 of the kidney was excised, and the rats were intraperitoneally injected with 25 mg/kg Streptozotocin (STZ, manufactured by Sigma Chemical) dissolved in a citrate buffer, to generate rats with diabetic nephropathy.

After one week passed from the injection, using the degraded galactomannan prepared in Example 1 and the polyphenol compound prepared in Example 2, the diabetic nephropathy-induced rats were orally administered consecutively for 50 days with the compositions and the Test Groups shown in Table 4.

TABLE 4

| Test Group | Rats Used | Dose of Test Substance |
|---|---|---|
| Normal Group | Normal Rats | Water 1 g/kg BW/day |
| Control Group | Rats with Diabetic Nephropathy | Water 1 g/kg BW/day |
| GTP*[1] Group | Rats with Diabetic Nephropathy | Polyphenol Compound of Ex. 2 100 mg/kg BW/day |
| PHGG*[2] Group | Rats with Diabetic Nephropathy | Degraded Galactomannan of Ex. 1 100 mg/kg BW/day |

TABLE 4-continued

| Test Group | Rats Used | Dose of Test Substance |
|---|---|---|
| GTP + PHGG Group | Rats with Diabetic Nephropathy | Polyphenol Compound of Ex. 2 50 mg/kg BW/day + Degraded Galactomannan of Ex. 1 50 mg/kg BW/day |

*[1]GTP is an abbreviation for green tea polyphenol.
*[2]PHGG is an abbreviation for partially hydrolyzed guar gum.

Figure 1:
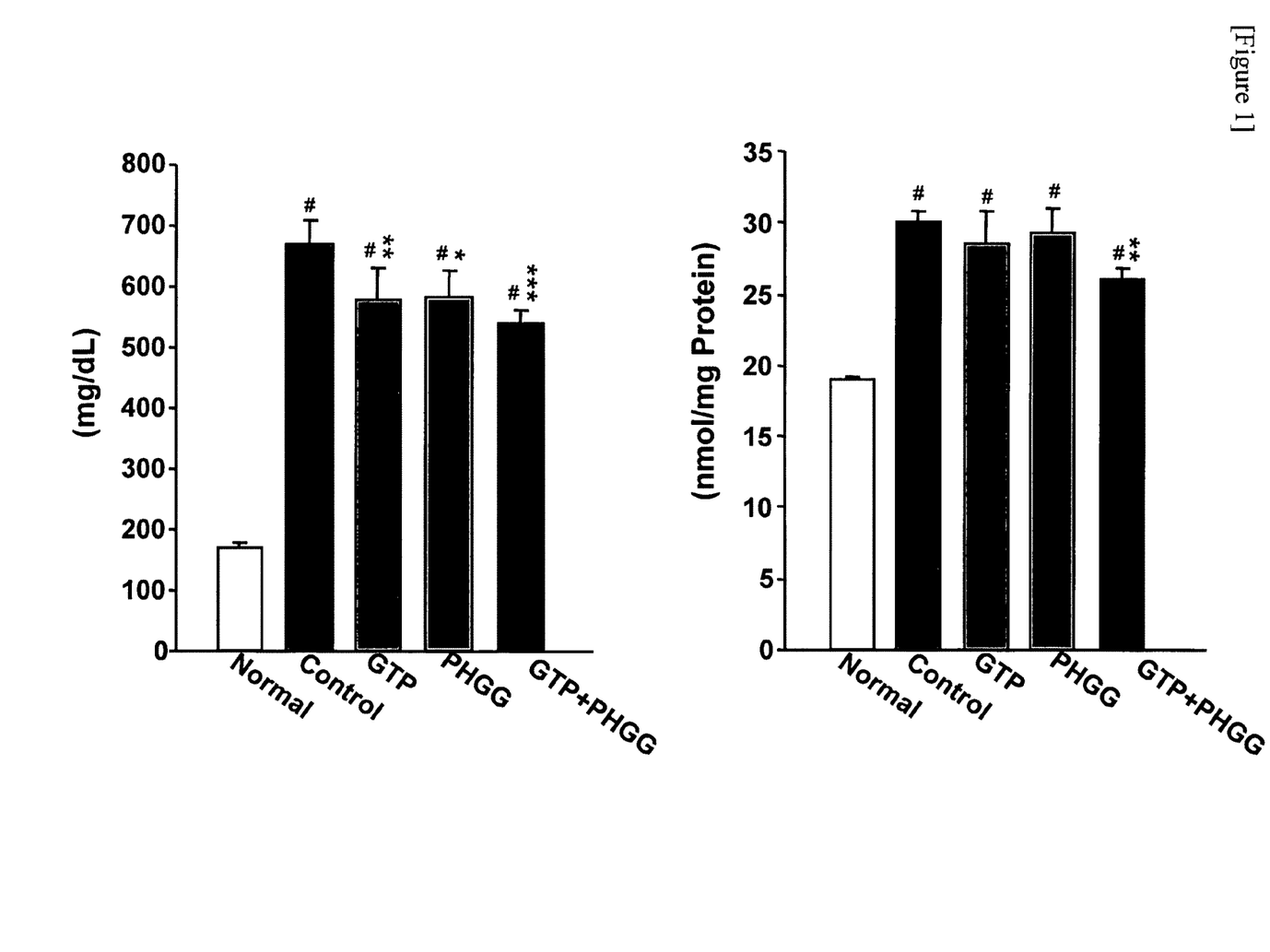
FIG. 1 is graphs for comparing the parameters relating to diabetic nephropathy, wherein the graph on the left side shows glucose, and the graph on the right side shows glycosylated protein. In the graphs, # is a case where $p<0.001$ for normal rats; * is a case where $p<0.05$ for control rats with diabetic nephropathy;  is a case where $p<0.01$ for control rats with diabetic nephropathy; and * is a case where $p<0.001$ for control rats with diabetic nephropathy.
Figure 2:
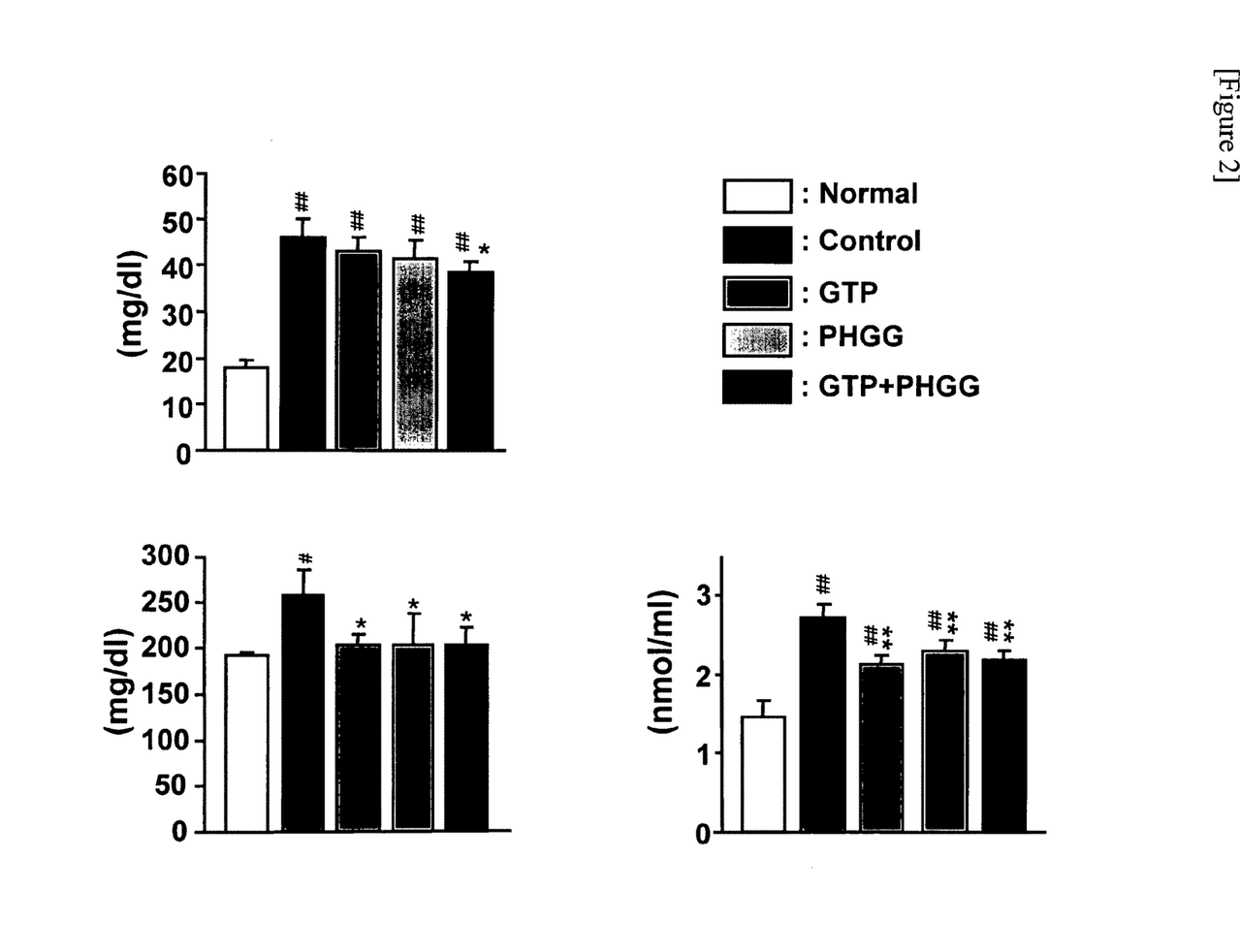
FIG. 2 is graphs for comparing the parameters relating to diabetic nephropathy, wherein the graph on the upper left side shows urea nitrogen, the graph on the lower left side shows triglyceride, and the graph on the right side shows MDA. In the graphs, # is a case where $p<0.01$ for normal rats; ## is a case where $p<0.001$ for normal rats; * is a case where $p<0.01$ for control rats with diabetic nephropathy; and ** is a case where $p<0.001$ for control rats with diabetic nephropathy.
Figure 3:
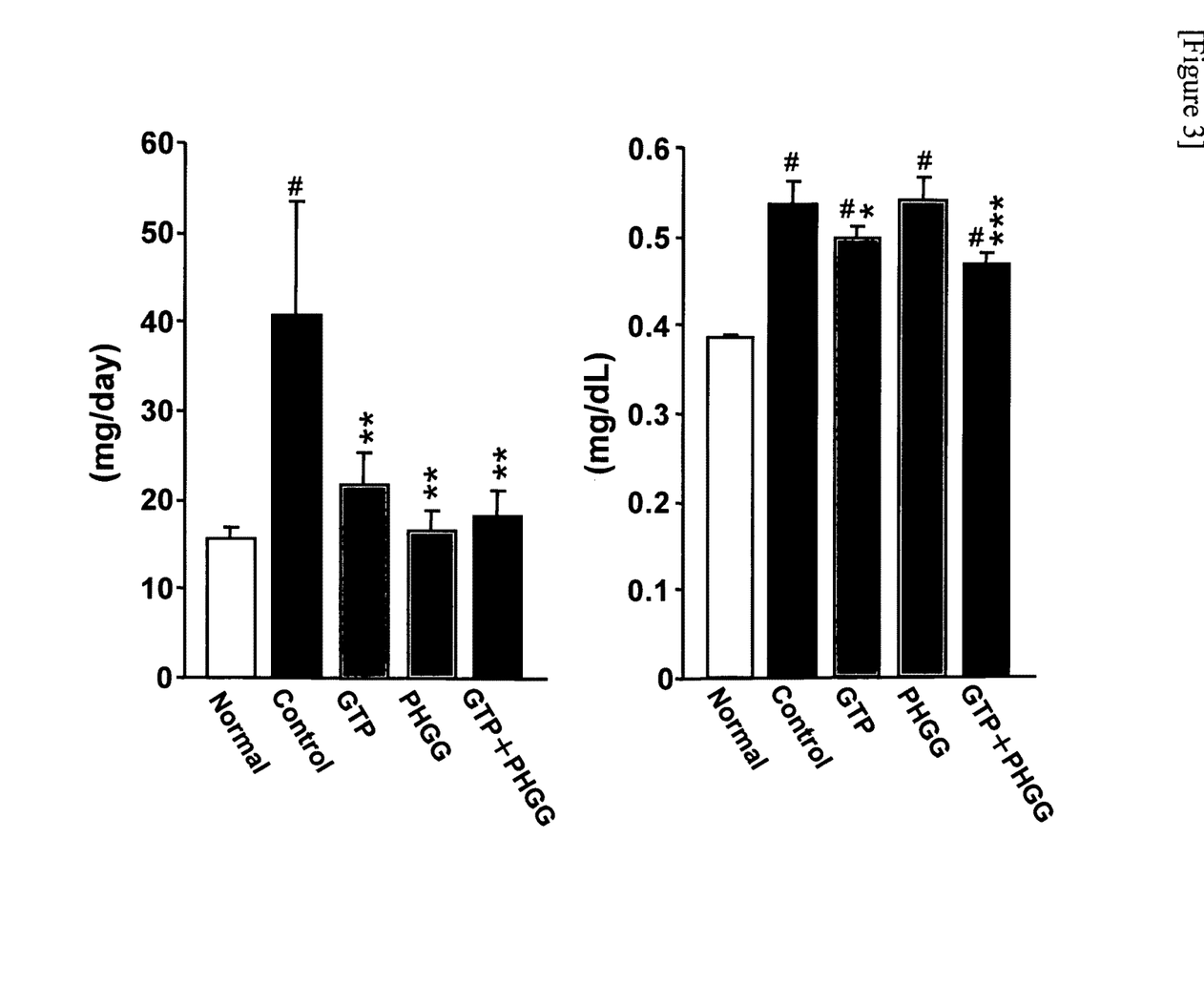
FIG. 3 is graphs for comparing the parameters relating to diabetic nephropathy, wherein the graph on the left side shows urinary protein, and the graph on the right side shows serum creatinine. In the graphs, # is a case where $p<0.001$ for normal rats; * is a case where $p<0.01$ for control rats with diabetic nephropathy; and ** is a case where $p<0.001$ for control rats with diabetic nephropathy.

On the fiftieth day from the administration of the test substance, blood was collected, sera were separated, and the glucose concentration level, the amount of glycosylated protein, the urea nitrogen concentration level, the triglyceride concentration level, the MDA concentration level, and the creatinine concentration level, each in the sera, were determined. In addition, on the fiftieth day from the administration of the test substance, urine of the rats was collected, and the amount of urinary protein was determined. The results are shown in FIGS. 1 to 3.

Here, the amount of the glycosylated protein and the creatinine concentration level were determined in the same manner as in Test Example 1. The glucose concentration level, the urea nitrogen concentration level, the triglyceride concentration level, the MDA concentration level, and the urinary protein were determined in the following manner.

Glucose Concentration Level

The glucose concentration level was determined with Glucose B Test Kit (manufactured by Wako Pure Chemicals Industries, Ltd.).

Urea Nitrogen Concentration Level

The urea nitrogen concentration level was determined with A/G B Test Wako (manufactured by Wako Pure Chemicals Industries, Ltd.).

Triglyceride Concentration Level

The triglyceride concentration level was determined with TRIGLYCERIDE E-Test Wako (manufactured by Wako Pure Chemicals Industries, Ltd.).

MDA Concentration Level

Malondialdehyde in blood and thiobarbituric acid were reacted, and the MDA concentration level was determined with a spectrophotometer (manufactured by Shimadzu Corporation) at an absorption wavelength for red color, 595 nm.

Amount of Urinary Protein

The amount of urinary protein was determined by nephelometric method using sulfosalicylic acid.

As shown in FIGS. 1 to 3, the GTP+PHGG Group showed lowering in the glucose concentration level, the amount of glycosylated protein, the urea nitrogen concentration level, the triglyceride concentration level, the MDA concentration level, the amount of urinary protein, and the creatinine concentration level; the GTP Group showed lowering in the glucose concentration level, the triglyceride concentration level, the MDA concentration level, the amount of urinary protein, and the creatinine concentration level; and the PHGG Group showed lowering in the glucose concentration level, the triglyceride concentration level, the MDA concentration level and the amount of urinary protein, all of Groups showing ameliorative effects on diabetic nephropathy as compared to the control.

After the above-mentioned determinations, the kidney of the rats was excised, and histopathological changes were observed in the mesangial region of the renal glomeruli of the kidney with an optical microscope (manufactured by NIKON). Microphotographs of the renal glomeruli of rats are shown in FIG. 4.

Figure 4:
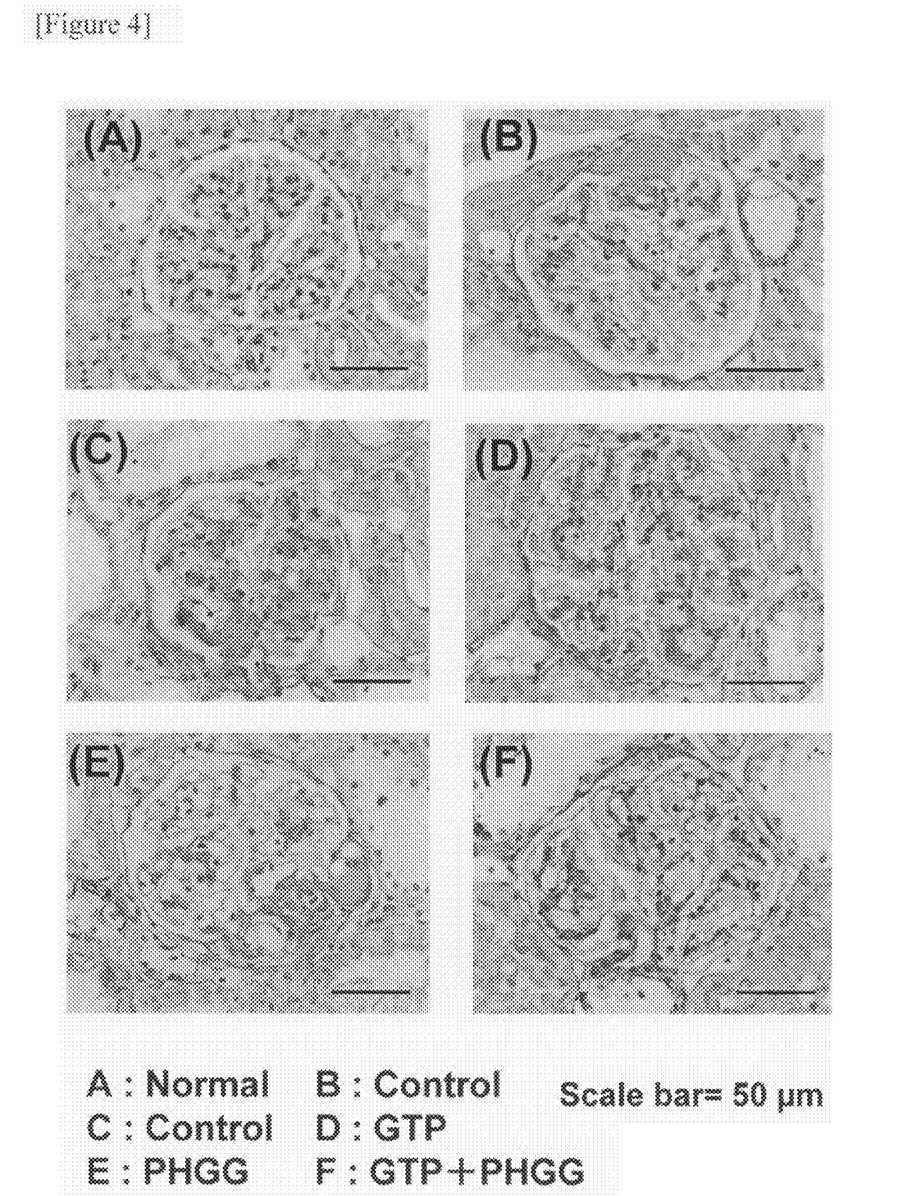
FIG. 4 is micrographs of glomeruli of diabetic nephropathy-induced rats.

From the microphotographs, while diabetic nephropathy-resembling glomeruli lesions, such as exudative lesion, arteriolosclerosis, and partly proliferation in mesangial substrate were observed in the control glomeruli ((B) and (C) of FIG. 4), the lesions as mentioned above were observed to be ameliorated in the glomeruli of the group administered with the composition of the present invention ((D), (E) and (F) of FIG. 4).

INDUSTRIAL APPLICABILITY

The composition of the present invention can be used in the prevention, amelioration, and treatment of diabetes mellitus and/or diabetic nephropathy.

The invention claimed is:
1. A method of treating diabetic nephropathy, comprising administering a composition comprising degraded galactomannan and a polyphenol compound to a subject in need thereof,
wherein the content of the degraded galactomannan in the composition is from 20 to 80% by weight and the content of the polyphenol compound in the composition is from 20 to 80% by weight
wherein 80% or more of the sugar chains constituting the degraded galactomannan has a degree of mannose polymerization of from 22 to 47 units and wherein the polyphenol compound is one or more compounds selected from (+)-catechin, (+)-gallocatechin, (−)-gallocatechin gallate, (−)-epicatechin, (−)-epicatechin gallate, (−)-epigallocatechin, (−)-catechin gallate, (−)-epigallocatechin gallate, gallic acid, free theaflavin, theaflavin monogallate A, theaflavin monogailate B, and theaflavin digallate.

* * * * *